(12) United States Patent
Gibson et al.

(10) Patent No.: US 9,035,256 B2
(45) Date of Patent: May 19, 2015

(54) GAS SENSOR WITH RADIATION GUIDE

(75) Inventors: Desmond Robert Gibson, Argyll & Bute (GB); Calum John MacGregor, Ayr (GB); Ewan MacKinnon Waddell, Stirlingshire (GB)

(73) Assignee: GAS SENSING SOLUTIONS LTD., Glasgow (GB)

( * ) Notice: Subject to any disclaimer, the term of this patent is extended or adjusted under 35 U.S.C. 154(b) by 366 days.

(21) Appl. No.: 13/522,831

(22) PCT Filed: Jan. 18, 2011

(86) PCT No.: PCT/GB2011/050077
§ 371 (c)(1),
(2), (4) Date: Oct. 10, 2012

(87) PCT Pub. No.: WO2011/086394
PCT Pub. Date: Jul. 21, 2011

(65) Prior Publication Data
US 2013/0026369 A1 Jan. 31, 2013

(30) Foreign Application Priority Data
Jan. 18, 2010 (GB) .................................. 1000756.5

(51) Int. Cl.
*G01J 5/02* (2006.01)
*G01N 21/3504* (2014.01)
*G01N 21/03* (2006.01)

(52) U.S. Cl.
CPC .......... *G01N 21/3504* (2013.01); *G01N 21/031* (2013.01); *G01N 2201/0636* (2013.01)

(58) Field of Classification Search
CPC .............................................. G01N 21/3504

USPC ......................................................... 250/343
See application file for complete search history.

(56) References Cited

U.S. PATENT DOCUMENTS 3,797,942 A   3/1974   Joly
4,557,603 A   12/1985  Oehler et al.
(Continued)

FOREIGN PATENT DOCUMENTS

CH   578176      5/1975
EP   0 647 845   4/1995
(Continued)

OTHER PUBLICATIONS

International Search Report for PCT/GB2011/050077 mailed May 25, 2011.
(Continued)

*Primary Examiner* — Kiho Kim
(74) *Attorney, Agent, or Firm* — Nixon & Vanderhye P.C.

(57) ABSTRACT

An optical absorption gas sensor includes a radiation source, detector and radiation guide which has a rectangular cross section and curves around a side of the cross section. Locating elements locate a support element relative to the radiation guide to align the radiation source and detector with the guide. Radiation from the reference radiation source may be transmitted through a transparent measurement radiation source. Radiation from a reference radiation source may be directed around the measurement reference source. A light emitting diode may generate radiation which is detected by a photodiode and the photodiode may be driven to generate radiation having a different emission spectrum detectable using the light emitting diode, in another operating mode. Two or more abutting L-shaped radiation guide portions may form the radiation guide.

43 Claims, 10 Drawing Sheets

(56) References Cited

U.S. PATENT DOCUMENTS

| | | | |
|---|---|---|---|
| 4,700,079 | A | 10/1987 | Ito |
| 4,756,622 | A | 7/1988 | Wong |
| 5,050,608 | A | 9/1991 | Watanabe et al. |
| 5,060,508 | A | 10/1991 | Wong |
| 5,163,332 | A | 11/1992 | Wong |
| 5,170,064 | A | 12/1992 | Howe |
| 5,340,986 | A | 8/1994 | Wong |
| 5,392,114 | A | 2/1995 | Cole |
| 5,453,620 | A | 9/1995 | Wadsworth et al. |
| 5,488,227 | A | 1/1996 | Sweet |
| 5,610,400 | A | 3/1997 | Weckström |
| 5,689,114 | A | 11/1997 | Miyazaki et al. |
| 5,696,379 | A | 12/1997 | Stock |
| 5,747,808 | A | 5/1998 | Wong |
| 5,834,777 | A | 11/1998 | Wong |
| 5,917,417 | A | 6/1999 | Girling et al. |
| 5,973,326 | A | 10/1999 | Parry et al. |
| 6,010,665 | A | 1/2000 | Dosoretz et al. |
| 6,016,203 | A | 1/2000 | Martin |
| 6,177,672 | B1 | 1/2001 | Lin et al. |
| 6,527,398 | B1 * | 3/2003 | Fetzer ............... 356/437 |
| 7,214,939 | B1 | 5/2007 | Wong |
| 7,488,942 | B2 | 2/2009 | Hopkins et al. |
| 8,368,895 | B2 | 2/2013 | Martin |
| 2002/0011568 | A1 | 1/2002 | Diekmann |
| 2002/0092974 | A1 | 7/2002 | Kouznetsov |
| 2005/0180889 | A1 | 8/2005 | Martin |
| 2006/0138328 | A1 | 6/2006 | Hopkins et al. |
| 2006/0290934 | A1 | 12/2006 | Boekelman |
| 2007/0120057 | A1 | 5/2007 | Tsai et al. |
| 2007/0145275 | A1 | 6/2007 | Wong |
| 2008/0035848 | A1 | 2/2008 | Wong |
| 2009/0235720 | A1 | 9/2009 | Smith |
| 2010/0006761 | A1 * | 1/2010 | Johnson et al. ............... 250/343 |

FOREIGN PATENT DOCUMENTS

| | | |
|---|---|---|
| EP | 0 825 430 | 2/1998 |
| EP | 0 826 957 | 3/1998 |
| EP | 1 818 667 | 8/2007 |
| GB | 1 502 687 | 3/1978 |
| JP | 60-69536 | 4/1985 |
| JP | 7-36051 | 7/1995 |
| JP | 7-198600 | 8/1995 |
| JP | 09-184803 | 7/1997 |
| JP | 9-229858 | 9/1997 |
| JP | 2005-337875 | 12/2005 |
| JP | 2005-337879 | 12/2005 |
| JP | 2006-300738 | 11/2006 |
| JP | 2007-506966 | 3/2007 |
| WO | WO 93/11418 | 6/1993 |
| WO | WO 97/18460 | 5/1997 |
| WO | WO2004/010116 | 1/2004 |

OTHER PUBLICATIONS

M. Haigh et al., "Mid-InfRARED AlxIn1—xSb Light-Emitting Diodes", Applied Physics Letters, AIP, American Institute of Physics, vol. 90, No. 23, Jun. 11, 2007, pp. 231116-231116.

Park, et al., Conference Proceedings of the 23rd Annual International Conference of the IEEE Engineering in Medicine and Biology Society: "Implementation of Gas Sampling Chamber and Measuring Hardware for Capnograph System Considering Thermal Noise Effect and Time Response Characteristics". Oct. 25-28, 2001, vol. 4, p. 3296-3299.

John U. White, "Long Optical Paths of Large Aperture". Journal of Optical Society of America, vol. 32, p. 285, May 1942.

* cited by examiner

GAS SENSOR WITH RADIATION GUIDE

This application is the U.S. national phase of International Application No. PCT/GB2011/050077 filed 18 Jan. 2011 which designated the U.S. and claims priority to GB 1000756.5 filed 18 Jan. 2010, the entire contents of each of which are hereby incorporated by reference.

FIELD OF THE INVENTION

The invention relates to the field of optical absorption gas sensors, including but not limited to infra-red absorption gas sensors.

BACKGROUND TO THE INVENTION

Gas sensors are commonly employed in industrial and consumer applications to measure analytes in the gaseous state. Many gas sensors rely on the absorption characteristics of the target analyte when illuminated with radiation and comprise a radiation source, a detector capable of detecting radiation emitted by the radiation source, and a chamber for receiving the target gaseous analyte. Analyte gas within the chamber absorbs radiation of specific wavelengths or ranges of wavelengths and the attenuation of the radiation detected by the detector gives an indication of the concentration of the target analyte within the chamber. The target analyte typically diffuses into the chamber although sensors which actively transport gas into the chamber are known. In some optical absorption gas sensors, the source emits radiation at a broad range of wavelengths and a wavelength selective filter is provided at the detector, in which case the gas sensor is referred to as a non-dispersive sensor. In other optical absorption gas sensors, the source emits radiation of a defined wavelength or wavelength range or includes a filter which selects a specific wavelength band.

To achieve high sensitivity, it is desirable that the radiation has as long a mean path length as possible through the analyte, from the radiation source to the detector, such that the analyte absorbs a significant portion of the radiation, and that the radiation is not absorbed by any other processes within the sensor. For example, if the path between the radiation source and the detector is not linear, the radiation must be reflected to be directed to the detector. However, the reflecting surface will introduce optical loss from absorption and/or scatter and this optical loss will typically be significant in a low cost sensor. There is therefore a balance to be struck between increasing the number of reflections to increase path length and avoiding excessive attenuation of the emitted radiation by excessive reflections.

However, for many practical applications, it is desirable for gas sensors to be small, or to comply with standardised dimensions, resulting in generally short path lengths and corresponding low sensitivity. Thus, one aim of the present invention is to provide a gas sensor that has high sensitivity whilst being compact and suitable for cost-effective manufacture.

It is known to provide gas sensors having a straight hollow tubular radiation guide which extends between the radiation source and the detector and has a rectangular or other cross section. Radiation guides of this type guide radiation with a range of path lengths depending on the orientation at which radiation enters the radiation guide. Radiation which enters the radiation guide at a high angle of incidence to the walls of the radiation guide reflects many times and so is more highly attenuated than radiation which enters a straight rectangular radiation guide at an orientation close to the axis of the radiation guide.

It is known that for linear radiation guides increasing the size of the cross section decreases the number of reflections and therefore the absorption loss but results in poor collection efficiency. A better arrangement is to have the beginning and end of the waveguide shaped eg as compound parabolic collectors (CPCs). The effect of this is to transform the radiation field as it moves along the waveguide. At the source it has a large angular spread and relatively small spatial spread, midway it has a small angular spread but large spatial spread and at the detector again it has a large angular spread but small spatial spread. If chosen correctly this arrangement can significantly reduce the absorption due to multiple reflections.

The incorporation of a curved portion into a radiation guide can facilitate the provision of a longer path for radiation in a given volume than a radiation guide lacking curved portions. However, where a radiation guide curves, radiation falling on the curved walls of the guide results in greater angular spread without a reduction in spatial spread and consequently an increase in loss due to absorption in the multiple reflections. In particular, where radiation falls onto a curved wall, parallel radiation incident on the curved wall will not be parallel after reflection and so be dispersed. Some radiation will be incident on a curved wall with a greater angle of incidence than would be the case were the wall planar. Thus, where a radiation guide curves, some radiation is reflected into a path where it reflects at a relatively high angle towards an opposite wall, with the effect that a substantial proportion of radiation entering a curved radiation guide may be reflected many times and so be strongly absorbed.

Furthermore, in embodiments comprising a curved radiation guide and a collector at the detector, the collimator is unable to direct the radiation onto the detector due to the increase in angular spread. Therefore, the intensity of radiation incident upon the detector is reduced, correspondingly reducing the sensitivity of the gas sensor.

Some aspects of the invention aim to provide optical absorption gas sensors with improved curved radiation guides which better transmit radiation from a radiation source to a detector through a gas sample.

Another problem which arises in the field of absorption gas sensors is that during operation the radiation source, which is often an infra-red radiation emitter, and the detector are temperature sensitive. The emission spectrum of the radiation source may vary with temperature and the sensitivity of the detector may also vary with temperature. As well as being affected by ambient temperature, the radiation source in particular will heat up in use. If the radiation output is to be substantial and pulsed, temperature may fluctuate dramatically. When measuring small attenuations, small measurement errors due to temperature fluctuations in either or both the source and the detector can create substantial errors in measured gas concentration.

WO 2007/091043 (Gas Sensing Solutions Limited) discloses a sensor in which an infra-red light emitting diode (functioning as radiation source) and a photodiode (functioning as detector) are located adjacent to each other and in thermal communication with each other. By locating the source and detector adjacent to each other and in thermal communication, they remain at substantially the same temperature, simplifying the procedure of compensating for temperature variation. Accordingly, some embodiments of the invention aim to provide a compact gas sensor having high sensitivity given the constraint that the source and detector should be either or both adjacent either other and in thermal communication.

Optical absorption gas sensors typically include a mechanism for providing a reference signal, in addition to a measurement signal, to enable more accurate measurement. One mechanism for obtaining a reference signal in a non-dispersive optical absorption sensor is to provide a second detector, with a different filter, to measure light at a wavelength which is not absorbed by any gas which is expected to be present in varying amounts. However, this adds to the complexity of the gas sensor, and therefore its cost. It is known to provide separate measurement and reference radiation sources, but there will typically be different paths between these sources and the detector, or the presence of a reference radiation source will require an optical arrangement which directs a lower proportion of emitted radiation to the detector than would be the case without the presence of a second radiation source. Accordingly, some aspects of the invention aim to provide improved or alternative mechanisms for obtaining a reference signal in an optical absorption gas sensor.

SUMMARY OF THE INVENTION

According to the first aspect of the invention there is provided a gas sensor comprising a radiation source, a detector operable to detect radiation emitted by the radiation source and a radiation guide operable to guide radiation between the radiation source and the detector, the radiation guide comprising a curved portion having a substantially rectangular cross section, wherein the curved portion of the radiation guide curves around an axis parallel to one of the sides of the rectangular cross section.

The substantially rectangular cross section may be a substantially square cross section (for example, a square cross section), but preferably the rectangular cross section is a substantially oblong cross section (for example, an oblong cross section) having a major and a minor dimension.

As the curved portion has a substantially rectangular cross-section and curves around an axis parallel to one of the sides of the rectangular cross-section, the angular spread of the radiation will be increased and some radiation will be reflected into paths where it is will be reflected many times (and thereby highly attenuated in a radiation guide which significantly absorbs incident radiation). However, this effect will occur in only one plane. Radiation which reflects off the walls which are normal to the axis around which the radiation guide curves will not be dispersed in this way. Thus, the amount of radiation which reaches the detector is greater than would be the case if the radiation guide did not have a rectangular cross section and curved around an axis parallel to one of the side of the rectangular cross section.

Preferably, the radiation guide comprises a collimator operable to at least partially collimate radiation emitted by the radiation source. Typically, the collimator reduces the angular spread of radiation more in an axis parallel to the major dimension than an axis parallel to the minor dimension of the radiation guide.

Preferably, the radiation guide comprises a condenser operable to condense radiation onto the detector.

The curved portion of the radiation guide increases the angular spread of the radiation in the plane of curvature only. Therefore, there is a disparity in angular spread for radiation reflected predominantly by the walls parallel to the minor dimension of the rectangular cross section and radiation reflected predominantly by the walls parallel to the major dimension of the rectangular cross section incident upon the condenser. The direction radiation incident to the condenser is condensed is determined by the angular spread of that radiation. Generally, the condenser will be optimised to direct radiation with the lower angular spread onto the detector. Therefore, radiation reflected predominantly by the walls parallel to the major dimension of the rectangular cross section, having a high angular spread, may not reach the detector.

Radiation having a high angular spread before being reflected within a curved radiation guide can be collected more efficiently by a condenser than collimated radiation having a low angular spread.

Therefore, in the present aspect of the invention, the collimator typically collimates the radiation emitted by the radiation source to a greater degree in the axis parallel to the major dimension of the rectangular cross section where reflections from the walls perpendicular to this axis will not generally introduce angular spread, and to a lesser degree in the axis parallel to the minor dimension of the rectangular cross section where reflections from the walls perpendicular to this axis will generally introduce angular spread.

Accordingly, the current aspect of the invention combines a long path length provided by a curved portion of the radiation guide and a high proportion of radiation emitted by the radiation source reaching the detector, leading to high sensitivity.

The curved portion of the radiation guide may curve around an axis parallel to the minor dimension of the substantially rectangular cross section. However, preferably, the curved portion of the radiation guide curves around an axis parallel to the major dimension of the substantially rectangular cross section. Thus, for a given cross-sectional area (and therefore volume of gas through which radiation passes) dispersion and attenuation will be less than would be the case if the curvature was around an axis parallel to the minor dimension or if the radiation guide has a substantially square cross section.

Preferably, the radiation guide, and the curved portion of the radiation guide, comprises a hollow tube. The interior of the radiation guide is in gaseous communication with air adjacent the gas sensor. Analyte gas is received within the hollow tube in use, through one or more apertures or gas permeable regions of the radiation guide. The radiation guide may have an inward facing surface formed from a material operable to reflect radiation emitted by the radiation source. The material may be a metallic coating, such as gold or aluminium. The material may be a dielectric coating. By enabling the use of materials which absorb some incident radiation the invention allow cost-effective sensors to be provided. Typically, the reflectivity of the material is at least 0.99, or typically at least 0.97.

The radiation source and the detector may be adjacent to each other. The spacing between the radiation source and the detector may be less than three times, and preferably less than two times, the mean breadth of the radiation guide in a plane extending through the radiation source and the detector (which may also be a plane of symmetry of the radiation guide). The shortest path length of radiation between the radiation source and the detector along the radiation guide is preferably at least 10 times (18 times in an example embodiment) the spacing between the radiation source and the detector. Thus, a significant path length is obtained while the radiation source and detector are close to each other.

The radiation source and the detector may be in thermal communication with each other, for example, directly or through heat transfer means. The radiation source and the detector may be in thermal communication so that, in use, the radiation source and the detector remain substantially in thermal equilibrium.

The gas sensor may comprise a support element, which may be a planar support, with the radiation source and detector mounted on the support element. The support element may comprise an electronic circuit and is typically a printed circuit board (PCB). The support element may further comprise heat transfer means operable to conduct heat between the radiation source and the detector. The heat transfer means may be the electrical circuit.

The radiation guide may comprise a plurality of said curved portions. The radiation guide may comprise first and second curved portions which curve in opposite senses. Preferably, the radiation guide comprises a first curved portion which curves in a first sense and then a second curved portion, further along the radiation guide than the first curved portion (measured from the radiation source to the detector) which curves in a second opposite sense. The radiation guide may further comprise a third curved portion, further along the radiation guide than the second curved portion (measured from the radiation source to the detector) curved in the first sense. This enables a longer radiation path to be provided in a given volume, particularly in embodiments where light is incident on the detector in generally the opposite direction to the direction at which light enters the radiation guide from the radiation source.

The radiation guide may comprise a first curved portion which curves in a first sense by at least 10°, and typically by at least 25°, and a second curved portion, further along the radiation guide than the first curved portion (measured from the radiation source to the detector) which curves in the opposite sense with a substantially constant curve for at least 180°. The first and second curved portions may be in direct contact with each other.

The radiation guide may extend substantially in a plane. The radiation guide may have a plane of symmetry. The curved portion of the radiation guide may curve within a plane.

The radiation guide may change the mean direction of radiation between the radiation source and the detector by at least 90°. The radiation guide may change the mean direction of radiation between the radiation source and the detector by at least 135°. In embodiments in which the detector receives radiation with a mean direction which is substantially opposite the mean direction at which radiation from the radiation source enters the radiation guide the radiation guide may change the mean direction of radiation between the radiation source and the detector by 160-200° and preferably 170-190° or more preferably 175-185°.

The integral of magnitude of the curvature of the radiation guide may be at least 90°, preferably at least 180° and more preferably at least 260°. The integral of the magnitude of the curvature of the radiation guide is preferably at least 90° greater than the net curvature of the radiation guide between the radiation source and the detector. Thus, it may be possible to provide a mean path length which is greater than if the radiation guide curved continuously in a single sense between the radiation source and the detector. Nevertheless, it may be that the integral of the magnitude of the curvature of the radiation guide is less than 720° or more preferably less than 540° to avoid excess attenuation of radiation.

The radiation guide may comprise a collimator operable to at least partially collimate radiation emitted by the source. By at least partially collimating radiation emitted by the source, the amount of light lost due to attenuation by multiple reflections in the curved portion of the radiation guide is reduced.

Preferably, the collimator is a partial collimator which partially reduces the angular spread of radiation. It is preferable for radiation to be directed through as much as possible of the volume of the radiation guide to maximise absorption by analyte gas. Furthermore, although radiation which is incident at a significant angle to the flat walls of the curved portion will be reflected a significant number of times, it will have a greater path length than radiation which is parallel to the flat walls of the curved portion. Accordingly, the collimator preferably partially collimates the radiation.

The collimator may be a reflector, for example, a parabolic reflector, and is typically part of the reflective interior surface of the radiation guide. At least part of the curved portion of the radiation guide may be at least part of the collimator. The collimator may be a lens or an array of lenses. Typically, the collimator has a substantially oblong cross section having a minor and a major dimension and the collimator reduces the angular spread of radiation more in an axis parallel to the major dimension than an axis parallel to the minor dimension. Preferably, the major dimension of the collimator and the major dimension of the or each curved portion of the radiation guide are parallel.

The collimator may extend for more than 5%, or preferably more than 10%, of the length of the radiation guide. We have found that collimators of this length provide a suitable degree of collimation for the present aspect of the invention.

The radiation guide may comprise a condenser operable to condense radiation onto the detector. The condenser may be a reflector, for example a parabolic reflector or an elliptical reflector. However, the condenser may comprise a lens or an array of lenses.

The condenser may extend for more than 5%, or preferably more than 10%, of the length of the radiation guide.

The or each curved portion of the radiation guide typically comprises an inner wall and an opposed outer wall such that the inner wall describes the inner arc of the curved portion and the opposed outer wall describes the outer arc of the curved portion. It may be that the inner wall of one or more said curved portions comprises an inlet to admit a gas sample into the radiation guide. Typically, less radiation falls on the inner wall of a curved portion of a radiation guide and, by providing an inlet for a gas sample in the inner wall of a curved portion of the radiation guide, the attenuation of radiation within the radiation guide by the inlet for a gas sample is less than would be the case if the inlet was provided in the outer wall. This is especially beneficial where the curved portion curves by more than 90° or preferably more than 180°.

The or each curved portion of the radiation guide may comprise an inward region and an outward region. The inner region of the radiation guide may correspond to that half of the radiation guide nearest the inner wall. The outward half of the radiation guide may correspond to that half of the radiation guide nearest the outer wall. Radiation travelling from the radiation source to the detector through the radiation guide may travel around the curved section of the radiation guide predominantly within the outward region of the radiation guide, as a result of the configuration of the radiation guide, the radiation source and the detector. This reduces the mean number of reflections of the radiation between the radiation source and the detector.

The width of the radiation guide may be less than one tenth the length of the radiation guide (measured along the centre of the radiation guide) but is preferably less than one twentieth the length of the radiation guide.

The gas sensor may comprise a radiation filter which selectively admits radiation within a defined wavelength range into the detector. The wavelength range is selected depending on the target analyte. Typically, the target analyte is a gaseous species such as $CO_2$, CO, NO, $CH_4$ or $NO_2$ etc.

The gas sensor may comprise a radiation filter which selectively admits radiation within a defined wavelength range at the radiation source.

The radiation source and or the detector may be chosen such that the radiation emitted or detected respectively coincides with a wavelength absorption peak of the target analyte to be detected.

The gas sensor may be a non-dispersive infra-red sensor. Typically, the majority of the radiation emitted by the radiation source is near infra red.

The radiation source may be a light-emitting diode (LED), an organic LED, a laser diode or another electrical component operable to convert electrical current into radiation. The radiation source may emit radiation in a broad spectrum of wavelengths. The radiation source may emit radiation in a narrow spectrum of wavelengths. Typically, the radiation source has a peak emission wavelength that overlaps with the absorption spectrum of the target analyte such that the target analyte may strongly absorb the radiation emitted by the radiation source.

The detector may be a photodiode. Alternatively, the detector may be a device operable to convert incident radiation into thermal energy and subsequently convert the thermal energy into electrical current. For example, the device may be a thermopile or pyroelectric detector.

The gas sensor may comprise a radiation guide element (comprising or consisting of the said radiation guide) and the abovementioned support element. The radiation guide element or the support element may comprise a plurality of locating elements configured to locate the support element relative to the radiation guide element (and to thereby align the detector and radiation source with the radiation guide). Some or all of the locating elements may comprise a protrusion or groove on the radiation guide element. In at least some cases, the support element may comprise a cooperating groove or protrusion respectively. Preferably, there will be three locating elements (formed in the radiation guide element or the support element). Typically there will be a cooperating groove or protrusion for two of the three locating elements (formed in the support element or radiation guide element respectively). This enables the relative movement of the radiation guide element and the support element to be fully constrained without being overconstrained.

The plurality of locating elements may comprise a pivot (e.g a protuberance received by a complementary recess) in the radiation guide element (or support element) around which the radiation guide element can be rotated relative to the support element during the process of locating the radiation guide element relative to the support element. The pivot may comprise a hemisphere or other protrusion.

The plurality of locating elements may comprise at least one protrusion (such as a post) in the radiation guide element (or support element) received by a complementary formation (for example, a groove) in the support element (or radiation guide element respectively) and configured to prevent rotation of the support element relative to the radiation guide element in the plane normal to the radiation guide. The complementary formation in the support element may be elongate. The elongate complementary formation may allow the support element or radiation guide element to expand (for example due to a rise in temperature) relative to the radiation guide element or support element respectively without relative rotation between the support element and the radiation guide element.

The plurality of locating elements may comprise at least one spacer. The at least one spacer may be located such that when the support element is mounted onto the radiation guide element the at least one spacer is between the detector and the radiation source. The at least one spacer may be configured to maintain a specified separation between the support element and the radiation guide element. The at least one spacer may be adapted to maintain a specified separation between the detector and the radiation source, and radiation guide of the radiation guide element.

Preferably, the at least one spacer is not received by a cooperating groove but abuts the opposing surface. For example, in embodiments where the spacer is located on the radiation guide element, the spacer abuts the support element and is not received by a cooperating groove.

The provision of a plurality of locating elements configured to locate the support element to the gas sensor allows the radiation source and the detector to be located precisely to the gas sensor such that the radiation source is adjacent to an aperture in the radiation guide and the detector is adjacent to an aperture in the radiation guide or to otherwise align the radiation source and detector relative to the radiation guide.

Preferably, the gas sensor comprises three locating elements. Preferably, the three locating elements comprise a pivot, a protrusion and a spacer. The three locating elements may be arranged to form the corners of a triangle, that is, with one of the locating elements located out of line with the other two.

Preferably, the gas sensor comprises biasing means (e.g. a biasing device) to bias the support element towards the radiation guide element. The biasing means may be a rigid or flexible element (such as a spring) which applies pressure onto the support element towards the radiation guide element. This enables the locating elements to constrain the relative position and orientation of the radiation guide element and the support element.

The provision of a biasing means ensures that the plurality of locating elements remain engaged with their respective cooperating grooves and surfaces, thereby ensuring that the support element is stably constrained against the radiation guide element, thus maintaining the alignment of the radiation guide and the detector with the radiation guide.

The radiation guide may comprise a support element facing surface. A recess may be formed in the support element facing surface adjacent to the radiation source. A recess may be formed in the support element facing surface adjacent to the detector. The recess formed in the support element facing surface adjacent to the radiation source and/or the detector may be located such that there is a separation between the radiation source and or the detector, and the support element facing surface of the radiation guide.

In embodiments of the invention where the radiation guide comprises a conductive surface (typically, a metal coating, for example, gold), provision of a recess formed in the support element facing surface adjacent to the radiation source and or the detector prevents an electrical short circuit being formed between the radiation guide and the radiation source or detector. This is applicable where the support element facing surface forms at least part of the conductive surface of the radiation guide. This is especially advantageous where the detector and/or radiation guide element has a radiation guide facing surface and an electrical connection (e.g. a connection to a wire extending to a circuit board) on the respective radiation guide facing surface.

According to a second aspect of the invention a gas sensor is provided comprising a radiation source, a detector operable to detect radiation emitted by the radiation source and a radiation guide operable to guide radiation between the radiation source and the detector, wherein the detector is operable to emit radiation having a different wavelength spectrum to that emitted by the radiation source, and the radiation source is operable to detect radiation emitted by the detector.

Preferably, the gas sensor may further comprise an electronic circuit operable to cause the radiation source and the detector to operate in two modes such that in a first mode the radiation source emits radiation and said radiation is detected by the detector to provide a measurement signal, and in a second mode the detector emits radiation and said radiation is detected by the radiation source to provide a reference signal.

Accordingly, the present aspect of the invention allows a reference signal and a measurement signal to be obtained along the same radiation path without the requirement of providing a separate radiation source and a separate detector. A gas sensor comprising a first and a second radiation source, and a first and a second detector will be larger than a gas sensor comprising a single radiation source and a single detector. Therefore, providing a radiation source and a detector that are each operable to emit radiation and to be sensitive to radiation emitted by the other enables the gas sensor of the present aspect of the invention to be smaller than gas sensors requiring an additional radiation source and detector.

Preferably, radiation emitted by the detector and detected by the radiation source provides a reference signal and the radiation emitted by the radiation source and detected by the detector provides a measurement signal. Typically the detector and radiation source emit radiation with different peak wavelengths. Typically, the radiation source emits radiation having a peak intensity at a wavelength substantially corresponding to a wavelength at which a target analyte gas absorbs radiation. Typically the detector emits radiation predominantly at wavelengths which are substantially less absorbed by a target analyte than the said wavelength of the peak intensity of radiation emitted by the radiation source.

Optional features described in relation to the first or second aspect of the invention are optional features of the second aspect of the invention and the gas sensor of the first aspect of the invention may also be a gas sensor according to the second aspect of the invention.

According to a third aspect of the invention there is provided a gas sensor comprising a first radiation source, a second radiation source, a detector operable to detect radiation emitted by the first radiation source and the second radiation source, and a radiation guide operable to guide radiation from the first radiation source and the second radiation source to the detector, wherein radiation emitted from the second radiation source is guided along a path extending either or both around or through the first radiation source.

Radiation detected from the first radiation source may be used to calculate a measurement or a reference signal in use. Radiation detected from the second radiation source may be used to calculate a reference or a measurement signal respectively. Thus, the second radiation source typically emits radiation with a different wavelength spectrum to the first radiation source.

Radiation emitted from the second radiation source may be guided along a path extending through the first radiation source. It may be that the substantial majority or all of the radiation from the second radiation source which reaches the detector passes through the first radiation source. Some or all of the said radiation is typically reflected from a radiation guide only after the radiation has passed through the first radiation source. The first radiation source may be located in the path extending from the second radiation source along the radiation guide to the detector. The first radiation source may be translucent at the peak wavelength emitted by the second radiation source. At least 1% of the radiation emitted by the second radiation source may be transmitted through the first radiation source, preferably at least 3%, and more preferably at least 10%.

Radiation emitted from the second radiation source may be transmitted around the first radiation source. The second radiation source may extend around the first radiation source. For example, the second radiation source may be annular.

The first and second radiation sources may be mounted to opposite sides of a printed circuit board. The printed circuit board may comprise a bore therethrough, with the first and second radiation sources located at opposite ends of the bore. The first radiation source may occlude the bore. The second radiation source may be oriented to direct light through the bore at least in part through the first radiation source. The second radiation source may be oriented to direct light through the bore and around the first radiation source.

The gas sensor may comprise an electronic circuit operable to pulse the first and second radiation sources. The first and second radiation sources may be pulsed alternately such that radiation from either the first radiation source or the second radiation source may be detected by the detector.

Accordingly, the output signal from the detector may be analysed to determine a measurement signal when the first radiation source is emitting and reference signal from the detector when the second radiation source is emitting. Therefore, both measurement and reference signals may be obtained from a single detector and processed to determine the measured concentration of analyte gas.

The gas sensor may further comprise a reference detector operable to detect radiation from the second radiation source, wherein the radiation guide further comprises directing means operable to direct radiation from the second radiation source to the reference detector and to prevent radiation from the second radiation source from being absorbed by the detector.

The directing means may comprise a dichroic reflector operable to reflect radiation emitted by the second radiation source and to transmit radiation emitted by the first radiation source.

Optional features described in relation to the first or second aspect of the invention are optional features of the third aspect of the invention and the gas sensor of the first aspect of the invention may also be a gas sensor according to the third aspect of the invention.

According to a fourth aspect of the invention there is provided an optical absorption gas sensor comprising a radiation source, a detector operable to detect radiation emitted from the radiation source and a radiation guide having a plurality of reflective walls, wherein the radiation guide is formed by two abutting radiation guide portions having substantially L-shaped reflective surfaces.

By substantially L-shaped reflective surfaces we refer to the shape of the reflective walls of the radiation guide portions in the plane perpendicular to the contact line of each abutment. Typically each substantially L-shaped reflective surface is defined by two planar reflective walls which meet at an angle of 80-100 degrees, and typically 90 degrees.

Typically, the reflective walls of the radiation guide portions comprise a reflecting coating on a substrate. The coating may comprise a metal, such as gold or aluminium, but may comprise two or more dielectric materials, such as $MgF_2$ and ZnS.

Optional features described in relation to the any previous aspect of the invention are optional features of the fourth aspect of the invention and the gas sensor of the first aspect of the invention may also be a gas sensor according to the fourth aspect of the invention.

According to a fifth aspect of the invention there is provided a method of manufacturing an optical absorption gas sensor comprising providing two radiation guide portions of the fourth aspect of the present invention and bonding the two radiation guide portions such that the two radiation guide portions abut each other to form a radiation guide with the reflective surfaces of the two radiation guide portions forming the interior surface of the radiation guide.

The radiation guide portions may comprise a single continuous elongate member comprising an L-shaped reflective surface. Alternatively, the radiation guide portions may comprise two elongate members bonded along an edge to form an L-shaped reflective surface.

Preferably, the material is a metal, such as gold or aluminium, but may comprise two or more dielectric materials, such as $MgF_2$ and $ZnS$.

Generally, radiation guides for gas sensors are manufactured by bonding a first planar member onto a second member comprising a trench to form a hollow body. Covering a planar surface with a material is straight forward and a uniform film can be readily produced. However, on a small length scale, it is technically challenging to produce a uniform film in a member comprising a trench.

Producing a uniform film on the inner surface of an L-shaped surface is much less technically challenging than for a member comprising a trench. Therefore, a higher quality film may be produced on an L-shaped surface and at lower expense than producing a uniform film in a trench.

Accordingly, the method of manufacture of the present aspect of the invention enables hollow bodies comprising a cavity, such as radiation guides and sample chambers, to be manufactured with uniform reflective films to a higher standard and for less expense than previous methods.

The invention extends in a sixth aspect to a gas sensor comprising a support element and a radiation guide element, the support element comprising a radiation source and a detector operable to detect radiation emitted by the radiation source; the radiation guide element comprising a radiation guide operable to guide radiation between the radiation source and the detector; wherein the support element or the radiation guide element comprise a plurality of locating elements configured to locate the support element relative to the radiation guide element to thereby align the radiation source and the detector with the radiation guide.

Typically, the gas sensor comprises three locating elements. The gas sensor may further comprise biasing means to bias the support element towards the radiation guide element. Further optional features of the gas sensor according to the sixth aspect of the invention correspond to those discussed above in relation to the first through fifth aspects of the invention.

The invention extends in a seventh aspect to a gas sensor comprising a support element and a radiation guide element, the support element comprising a radiation source and a detector operable to detect radiation emitted by the radiation source, the radiation guide element comprising a radiation guide having a conductive surface, the radiation source and/or detector having a radiation guide facing surface with an electrical connection on the radiation guide facing surface, the radiation guide comprising a support element facing surface which forms at least part of the conductive surface, and a recess in the support element facing surface adjacent to the radiation source and/or a recess in the support element facing surface adjacent to the detector. Further optional features of the gas sensor according to the sixth aspect of the invention correspond to those discussed above in relation to the first through fifth aspects of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
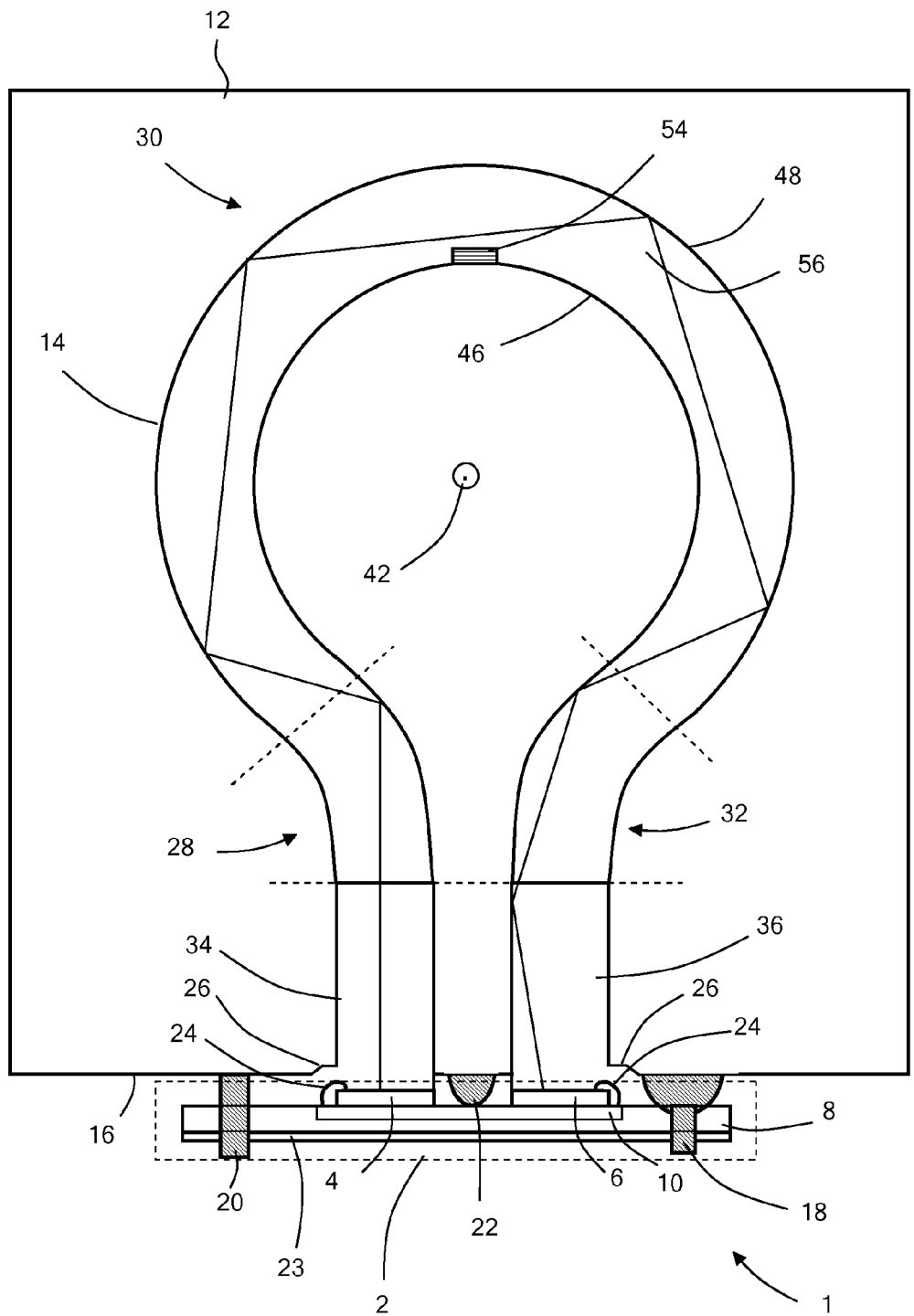
FIG. 1 is a plan view of a gas sensor illustrating the path of an example ray.
Figure 2:
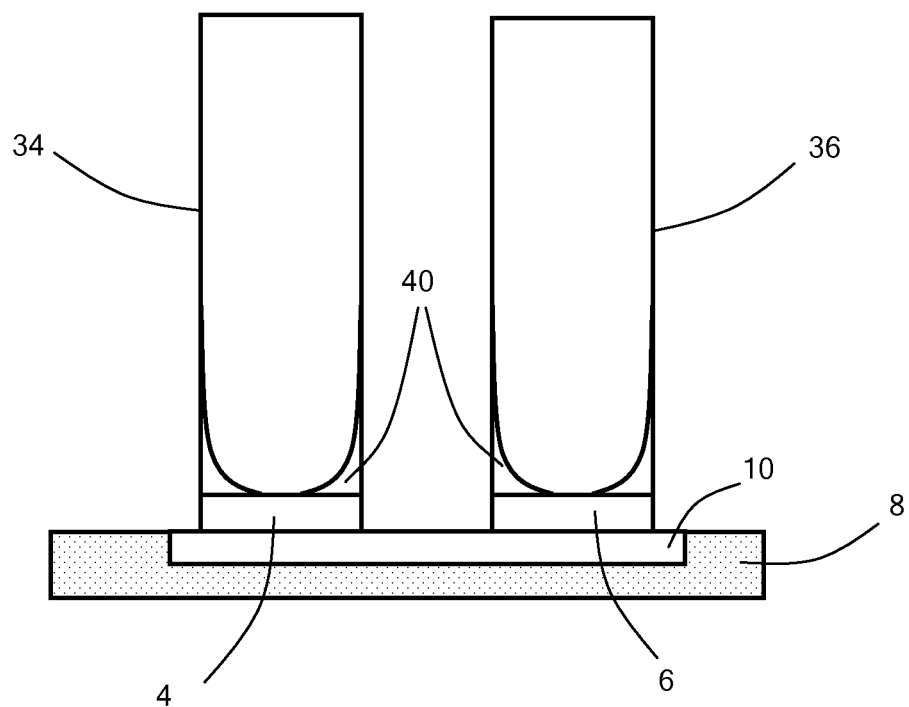
FIG. 2 illustrates the mounting for the radiation source and detector of the gas sensor.
Figure 3:
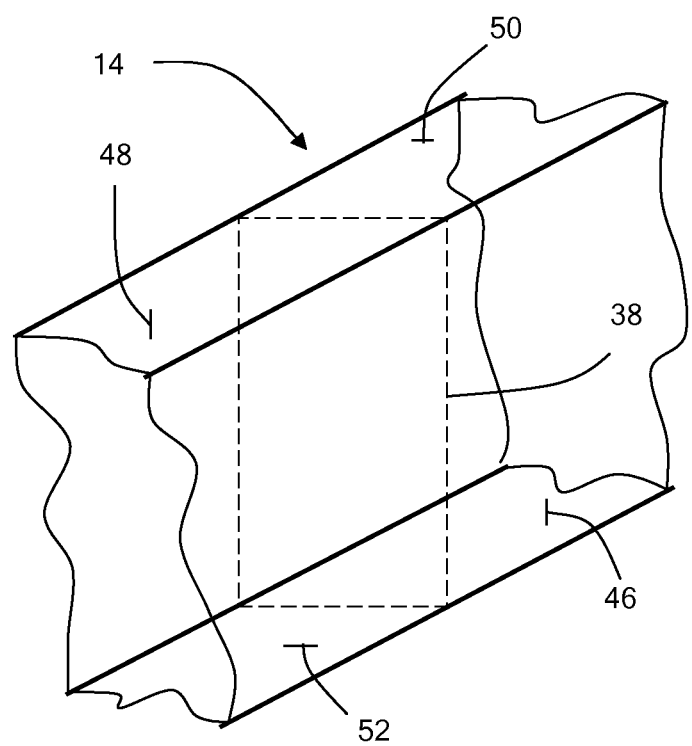
FIG. 3 is a plan view of the radiation guide of the gas sensor of FIG. 1, including traces of several example rays.

With reference to FIGS. 1 through 5, an optical absorption gas sensor 1 comprises a support (functioning as the support element) 2 including a light emitting diode 4 (functioning as the radiation source) and a mid infra-red emitting photodiode 6 (functioning as the detector), located adjacent to each other and mounted on a printed circuit board 8. Electronic circuitry 10 on the printed circuit board conducts heat between the light emitting diode and the photodiode, and thereby functions as heat conduction means.

The optical absorption gas sensor comprises body 12 (functioning as a radiation guide element) including a hollow tubular radiation guide 14. The body comprises a support facing surface 16. The support facing surface comprises a pivot 18, which acts as a first reference point, a post 20 which fits into a radial groove to prevent relative rotation of the body and the support while allowing some differential thermal expansion, and a spacer 22 (the pivot, post and spacer collectively functioning as the plurality of locating elements). The support is mounted to the body and located by the pivot, post and spacer such that the radiation guide extends from the light emitting diode to the photodiode, with the light emitting diode and photodiode aligned with the radiation guide.

The support further comprises a plate 23 (acting as a biasing means) which extends from the body around the support, and induces a force pulling the support towards the body, which is opposed by the pivot, post and spacer, thus ensuring that the pivot, post and spacer are fully engaged with the support, thereby maintaining the alignment of the light emitting diode and the photodiode with the radiation guide. The plate can be sprung, or rigid and simply held directly against the support. It may, for example, simply comprise holes for receiving the pivot and post and be attached using an interference fit.

The light emitting diode and photodiode are each front mounted, with exposed gold wires 24 extending from the surface of the printed circuit board to the surface of each device. The support facing surface further comprises two recesses 26. The first recess is located adjacent to the photodiode and the second recess is located adjacent to the light emitting diode. These recesses avoid the possibility of an electrical short through the wires and the gold reflecting surface of the radiation guide. The recesses are located only along the edges of the radiation guide where the wires are present and the radiation guide is preferably very close to or contacts the printed circuit board around the sides of the detector and photodiode which do not have an exposed wire.

The radiation guide has a reflective coating of gold, which absorbs 2 to 5% of the infra-red light which is incident on it, and reflects the remainder. The radiation guide includes a first curved portion 28, a second curved portion 30, and a third curved portion 32, a collimator 34, which tapers towards the light emitting diode, and a condenser 36 which tapers towards the detector. Although they are illustrated as separate regions of the radiation guide, the collimator and condenser will typically blend into the first and third curved portions respectively.

The radiation guide has a rectangular cross-section 38 throughout, except for parabolic reflectors 40 behind the light emitting diode and the photodiode. The minor dimension of the rectangular cross-section is in a plane extending through the light emitting diode, the photodiode, and the radiation guide (the same plane as the cross-section of FIG. 1), and the major dimension of the rectangular cross-section is perpendicular to this plane. The aspect ratio of the radiation guide where it has its greatest cross-section is typically between about 4:1 and about 8:1.

Figure 4:
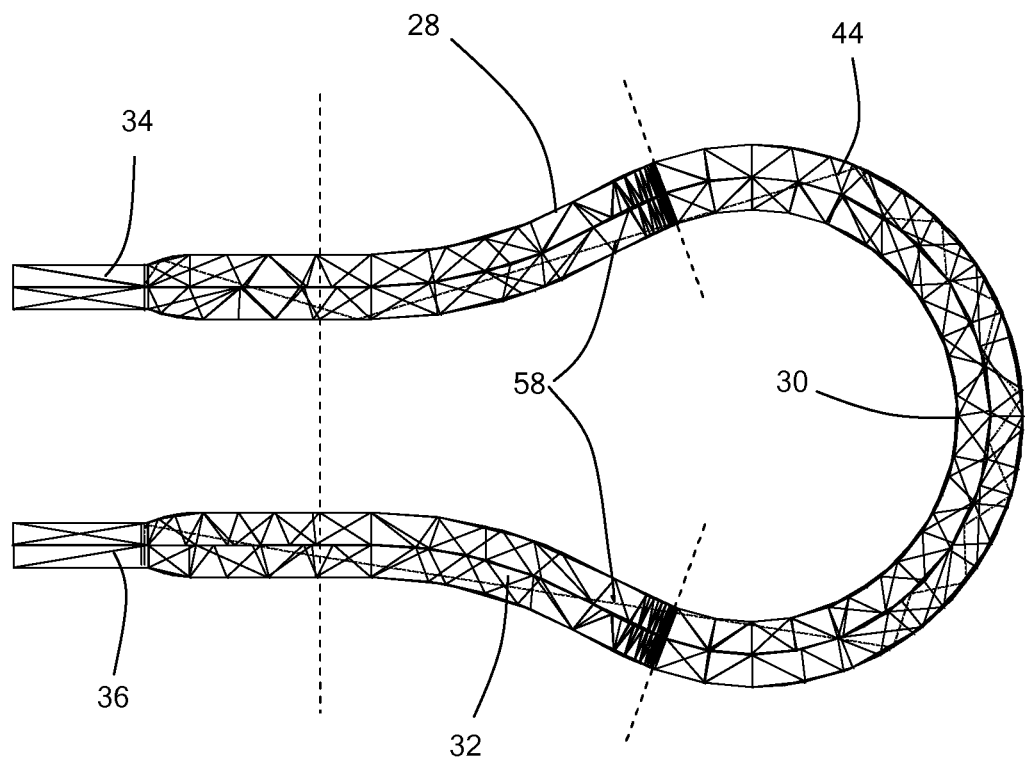
FIG. 4 is a perspective view of the radiation guide of the gas sensor of FIG. 1 including ray traces.
Figure 5:
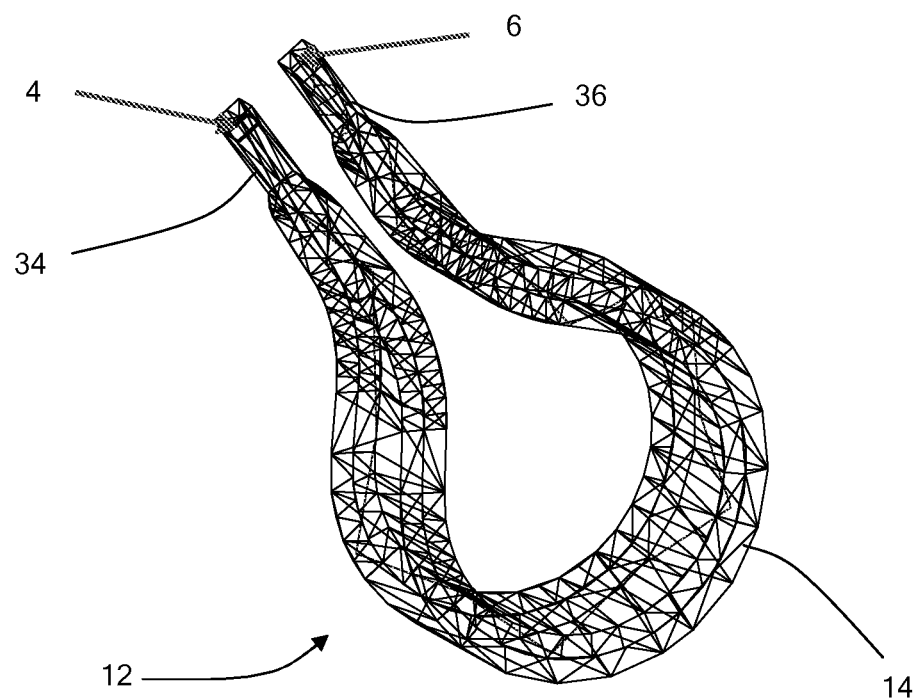
FIG. 5 is a perspective view of the radiation guide of the gas sensor of FIG. 1 including ray traces.

The radiation guide curves generally within the said plane. The first curved portion curves outwards. At any given point, it curves around an axis parallel to the major dimension of the rectangular cross-section, although the location of the axis around which it curves, and therefore the radius of curvature, may vary along the length of the first curved portion. The second curved portion curves in the opposite sense, again around an axis parallel to the major dimension of the rectangular cross-section. The second curved portion describes a part-circle, with a constant radius of curvature around an axis 42. The third curved portion again curves outwards, in the same sense as the first curved portion, and the opposite sense to the second curved portion. Radiation is guided around the curved portion by reflection and FIG. 4 illustrated example ray traces 44.

The radiation guide has an inner wall 46 and an outer wall 48 perpendicular to the plane of the sensor and opposing flats walls 50 and 52 parallel to the plane of the sensor. One more gas access points 54 are provided within the inner wall to enable a gas sample to diffuse into the cavity 56 defined by the walls of the radiation guide from the immediate surroundings of the gas sensor. The body of the sensor may comprise a dust exclusion grille or fabric covered channel (not shown) for gas to diffuse from the surroundings of the gas sensor to the or each gas access point.

The light emitting diode and photodiode are each formed from a narrow band gap III-V material indium aluminium antimonide material $((In_{1-x})Al_xSb)$, grown on a gallium arsenide (GaAs) substrate, the doping of which is chosen to tune the band gap to cause the light emitting diode to emit light of a narrow wavelength range corresponding to a wavelength at which gaseous carbon dioxide absorbs strongly. The formation of suitable light emitting diodes and photodiodes are disclosed in EP 0 864 180, EP 0 992 094, and in Haigh, M. K. et al., Applied Physics Letters, vol. 90, 231116 (2007), the contents of each of these documents being incorporated herein by virtue of this reference.

The light emitting diode and photodiode may be fabricated from the same semiconducting substrate. The light emitting diode and photodiode may also be fabricated from similar substrates and differ only in their epilayer thicknesses, which maybe tuned to enhance the performance of light emission in the case of the light emitting diode or collection in the case of the photodiode. Due to their proximity and the present of heat conduction means, the light emitting diode and photodiode will remain in thermal equilibrium, facilitating temperature compensation, for example, using a temperature compensation circuit set out in WO 2009/019467 (Gas Sensing Solutions Limited).

In use, the light emitting diode is driven by a conventional light emitting diode driving circuit. The light emitting diode emits electromagnetic radiation of a narrow band of wavelengths centred on 4.3 µm (in the case of a gas sensor for measuring carbon dioxide concentration). The radiation is emitted with a broad angular spread and a generally lambertian distribution. The radiation is partially collimated by the collimator and passes through the first, second and third curved portions of the radiation guide in turn. All radiation will be reflected at least several times. Due to the curvature in the plane of the radiation guide, some radiation will be reflected onto a path where it reflects many times between the opposing walls and so is substantially attenuated, for example ray 58. However, radiation which reflects off the walls which are generally parallel to the plane of the radiation guide will not change the component of its path in the plane of the radiation guide, avoiding the additional dispersion and attenuation which would arise if the walls which are generally parallel to the plane of the radiation guide were not flat.

Much of the radiation from the source will reflect several times off the walls which are generally parallel to the plane of the radiation guide. Thus, the mean path length between the light emitting diode and the photodiode is greater than would be the case if the radiation from the light emitting diode was sufficiently collimated to have only a narrow range of angles from the plane of the radiation guide. The condenser typically has the same profile as the collimator, except that it faces in the opposite direction.

The radiation guide changes the mean direction of emitted radiation by 180° between the light emitting diode and the detector, but the first curved portion curves by around 45°, the second curved portion curves by around 270° in the opposite sense, and the third curved portion curves by around 45° in the same sense as the first curved portion. Thus, the integral of the magnitude of the curvature of the radiation guide between the light emitting diode and the photodiode is around 360°. A relatively long gently curved radiation guide has been provided, enabling a relatively long mean path length to be achieved in a compact sensor.

Furthermore, as a result of the configuration of the radiation guide, a substantial proportion of radiation emitted by the light emitting diode will reach the photodiode provided that it is not absorbed by gas. The amount of radiation detected by the photodiode will depend on the concentration of gas within the radiation guide which absorbs radiation from the light emitting diode.

A gas sample enters and leaves the chamber within the radiation guide by diffusion through the gas access port. The gas access port is located on the inside surface of the second curved portion. Less radiation is incident on the inside surface than the outside surface. Thus, less radiation is lost due to absorption or scattering by the gas access port than would be the case if the gas access port was instead located on the outside surface of the second curved portion. Several gas access ports can be provided on the inside surface of the second curved portion, and possible also other curved portions. As the sensor is relatively compact, the rate at which the composition of gas within the radiation guide equilibrates with external gas (e.g. air) is relatively fast, providing a sensor with a relatively quick response to changing gas concentrations.

The sensor may be operated without a reference signal. However, it is preferable that a reference signal, which has only a low or no sensitivity to the concentration of analyte gas is also measured, and used to calibrate the measurement signal, to enable a more accurate measurement of analyte gas concentration to be obtained.

Two examples of alternative apparatus and methods for obtaining a suitable reference signal will now be described. Each of these apparatus and methods may be employed with the apparatus described above and illustrated with reference to FIGS. 1 through 5 and may also be employed with other types of optical absorption gas sensor having a radiation source and a detector sensitive to radiation from the radiation source.

Example 1

Figure 6:
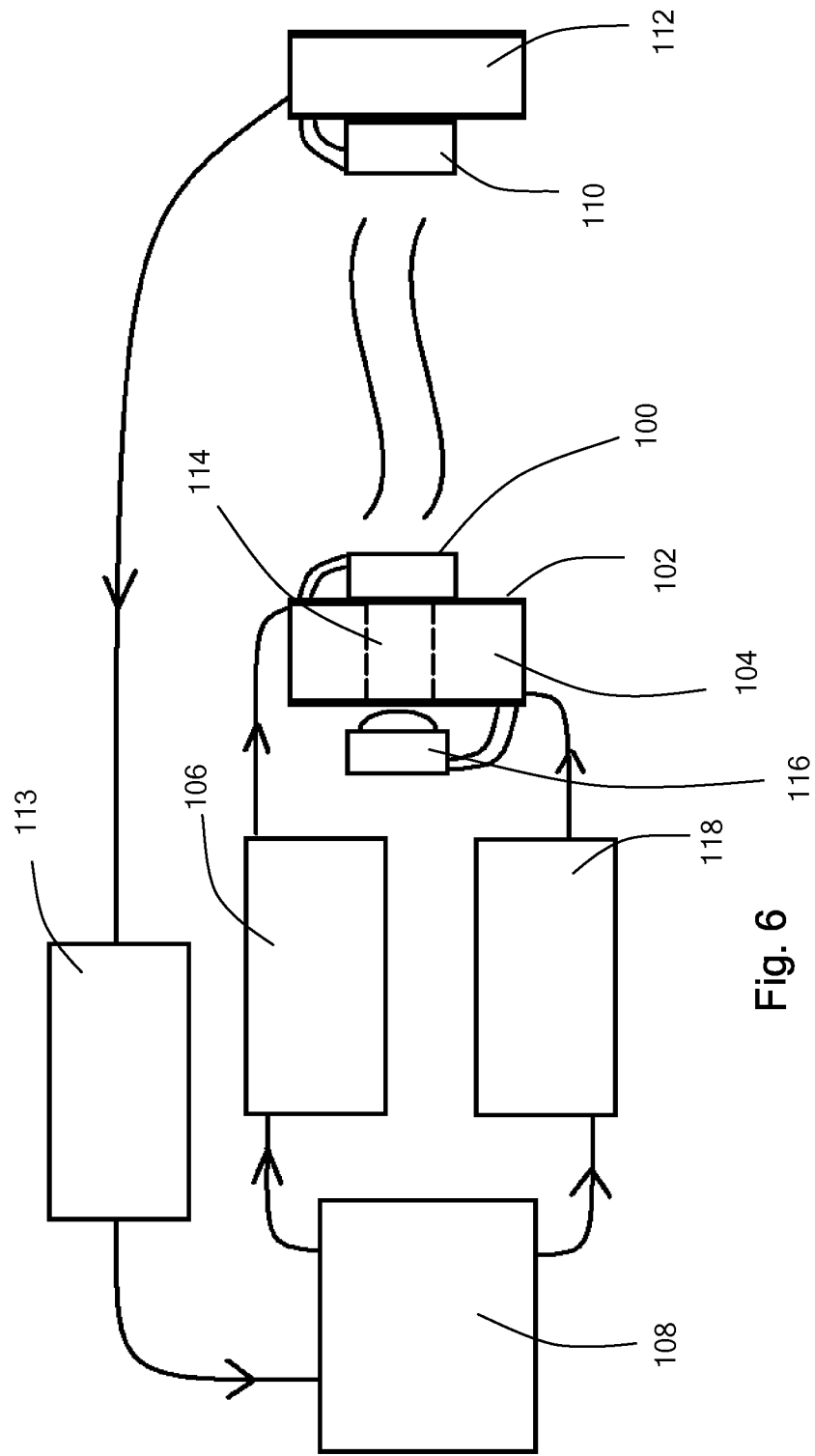
FIG. 6 is a schematic diagram of components of a first configuration for obtaining both a reference and measurement signal in a gas sensor.

With reference to FIG. 6, a first indium aluminium antimonide light emitting diode 100, which emits radiation with a peak intensity at around 4.3 µm in use, is provided on a first side 102 of a 1.6 mm thick fibreglass resin printed circuit board 104. The first light emitting diode is formed according to EP 0 864 180, EP 0 992 094, and in Haigh, M. K. et al., Applied Physics Letters, vol. 90, 231116 (2007). This first light emitting diode is driven by an electronic circuit 106, under control of a microcontroller 108 to provide electromagnetic radiation which is detected by a photodiode 110. The photodiode is also based on indium aluminium antimonide and is mounted to a printed circuit board 112 which, when used with the gas sensor of FIGS. 1 to 5, is preferably a region of the printed circuit board to which the first light emitting diode is mounted, adjacent the light emitting diode, to facilitate thermal communication between the light emitting diode and the photodiode through electronic circuitry printed on the printed circuit board.

The radiation guide illustrated in FIGS. 1 though 5 extends between the light emitting diode and the photodiode, to direct radiation from the light emitting diode through a sample gas so that the amount of radiation detected by the photodiode is sensitive to the concentration of gas which absorbs radiation at around 4.3 µm. Current from the photodiode is amplified by a photodiode amplifier circuit 113 and the resulting measurement is provided to the microcontroller.

Figure 7:
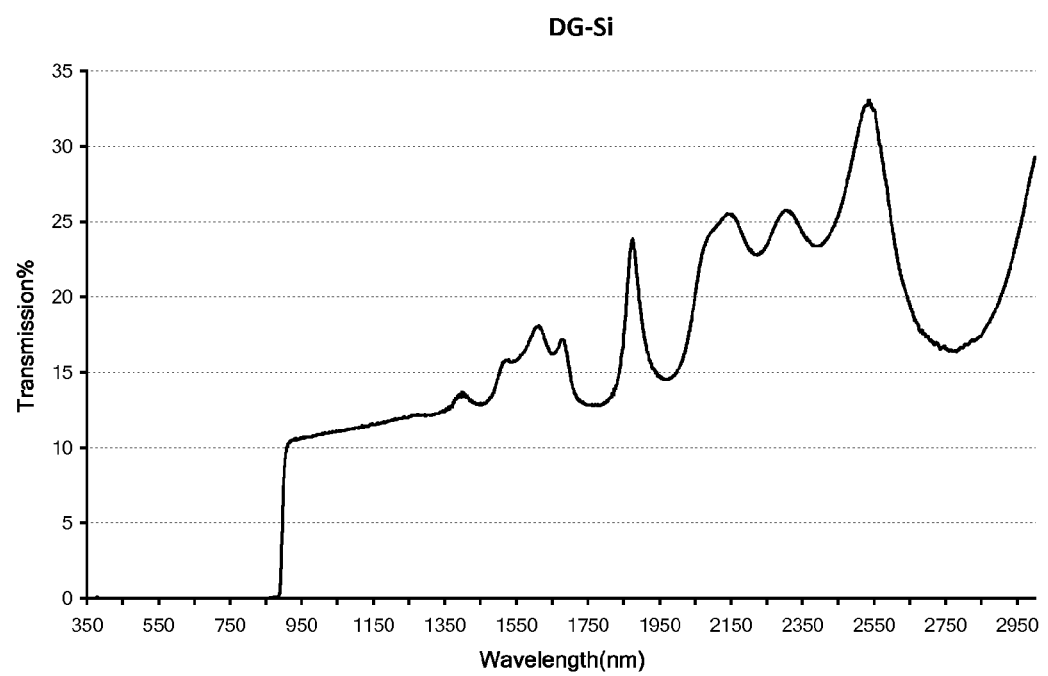
FIG. 7 is a graph of radiation transmission versus wavelength for an example light emitting diode.

The first light emitting diode includes a bore 114 which extends through the circuit board. A second light emitting diode 116, which emits electromagnetic radiation at a wavelength of 950 nm, is fixed to the opposite side of the circuit board to the first light emitting diode, and is oriented to direct emitted radiation through the bore. The first light emitting diode has an absorption spectrum illustrated in FIG. 7. The first light emitting diode transmits around 10% of radiation at a wavelength of 950 nm, and so is translucent to radiation of this wavelength. Although the photodiode is optimised to detect radiation of around 4.3 µm wavelength, it is also sensitive to some extent to radiation at 950 nm. Accordingly, radiation from the second light emitting diode can also be detected by the photodiode, and measured using the photodiode amplifier. A second light emitting diode drive circuit 118 is provided to drive the second light emitting diode, under the control of the microcontroller.

In use, the microcontroller signals the drive circuits for the first and second light emitting diodes so that the first and second light emitting diodes pulse alternately. Thus, the currents generated by the photodiode alternately provide a measure of radiation received from the first and second light emitting diodes in turn. Radiation at from the first light emitting diode, at a wavelength of around 4.3 µm is absorbed in dependence on the amount of carbon dioxide which is present and the intensity measured while the first light emitting diode is illuminated provides a measurement signal. Radiation emitted at 950 nm by the second light emitting diode is only absorbed minimally by carbon dioxide, and other gases typically found in the atmosphere, is low. Accordingly, the microcontroller can determine the concentration of carbon monoxide from the measurement signal while using the absorption of radiation emitted by the second light emitting diode to calibrate the measured signal.

Ideally, the second light emitting diode is chosen to have a similar response to temperature and other environmental factors to the first light emitting diode. The path for radiation from the second light emitting diode to the photodiode is the same as the path of a radiation from the first light emitting diode to the photodiode, although the angular spread of radiation through the first light emitting diode from the second light emitting diode may be different to the angular spread of radiation generated by the first light emitting diode. Nevertheless, this provides a useful calibration signal which can be employed to provide a more accurate measured gas concentration signal than would be possible using only a single light emitting diode.

In a variation of this strategy, rather than being transmitted through the first light emitting radiation source, radiation from the second radiation source may be reflected around the first radiation source, or a second radiation source may be provided which extends around the first radiation source. The first and second radiation sources are controlled as before.

Example 2

In a second, alternative approach for obtaining a reference measurement, we have found that an indium aluminium antimonide based photodiode will emit light when driven using a conventional light emitting diode driving circuit. Similarly, an indium aluminium antimonide-based light emitting diode according to EP 0 864 180, EP 0 992 094, and in Haigh, M. K. et al., Applied Physics Letters, vol. 90, 231116 (2007), referred to above, can be used as a photodiode by attachment to a conventional photodiode amplifier circuit.

Figure 8:
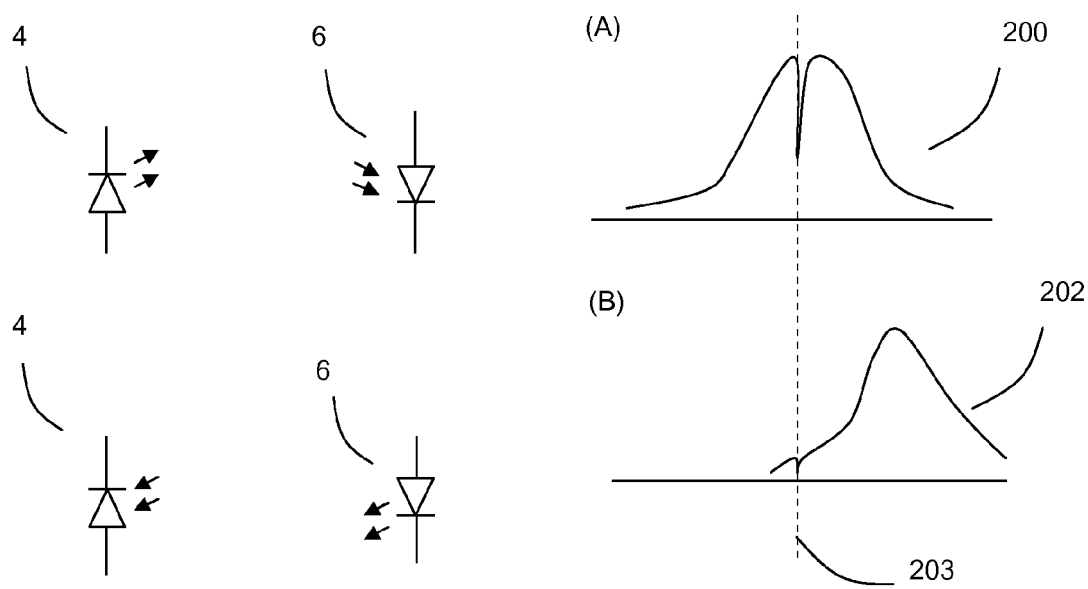
FIG. 8 illustrates the spectra of radiation emitted by (a) a light emitting diode; and (b) a photodiode, in a second configuration for obtaining both a reference and measurement signal in a gas sensor.

Thus, in the second example, a light emitting diode is pulsed, as before, and the current at the photodiode is measured to provide a measurement signal. Between each pulse of the light emitting diode, the photodiode is driven to emit radiation, and radiation received at the light emitting diode is measured using an amplifier. In this mode, the radiation emitted by the photodiode is predominantly at a significantly higher wavelength than the radiation emitted by the light emitting diode, and is much less sensitive to carbon dioxide concentration. The emission spectra of the light emitting diode 200 and the photodiode 202 are shown in FIGS. 8A and 8B.

Accordingly, the current generated by the photodiode when the light emitting diode emits radiation is used to derive a measurement signal and the current generated by the light emitting diode while the photodiode emits radiation is used to derive a reference signal. A microcontroller uses the reference signal to calibrate the measurement signal and then outputs a signal which is a more accurate measurement of carbon dioxide concentration than would be possible without the reference signal.

One skilled in the art will appreciate that the two examples of apparatus and methods for obtaining a reference measurement may be employed in any optical absorption gas sensor and not only an optical absorption gas sensor according to FIGS. 1 to 5.

Although the example optical absorption gas sensors disclosed herein are adapted for the detection of carbon dioxide, the sensors can be customised for the detection of different gaseous analytes by selecting radiation sources and detectors adapted to measure the attenuation of radiation having a wavelength or range of wavelengths corresponding to wavelengths at which the specific analytes absorb strongly but at which other components of air or potential interferents to do not absorb strongly.

Figure 9A:
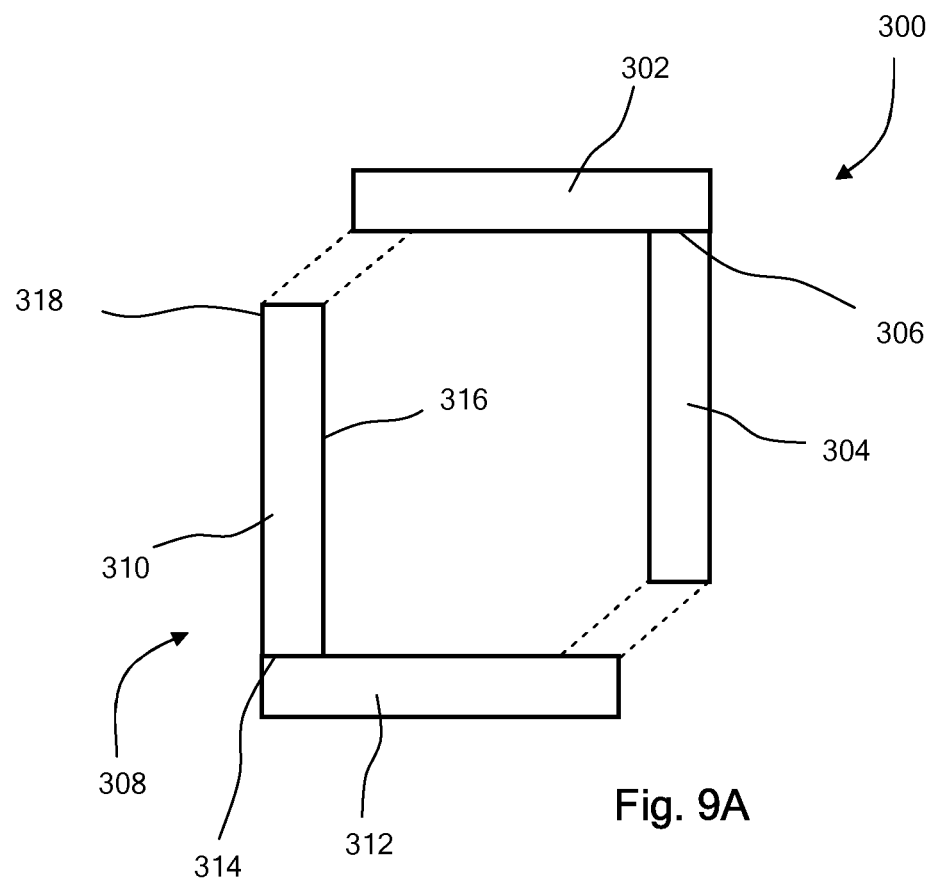
FIG. 9 illustrates a comparison of assembling a radiation guide from (A) two "L-shaped" bodies and from (B) a planar body and a trench-like body.
Figure 9B:
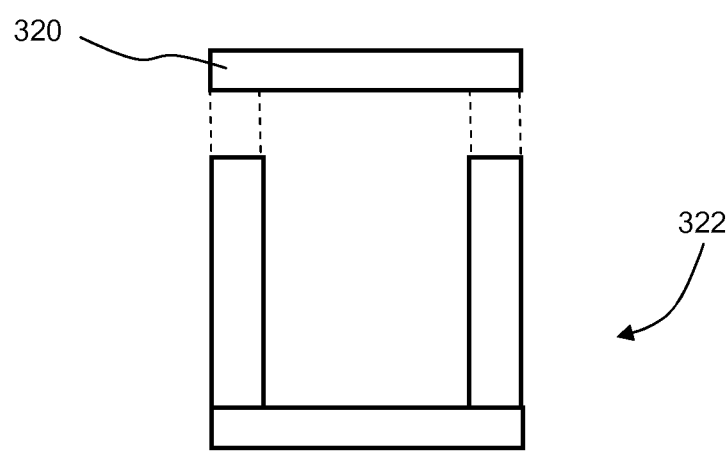

With reference to FIG. 9, an alternative embodiment of the present invention provides a method of manufacture for optical absorption gas sensors comprising a cavity. The example embodiment of a linear rectangular radiation guide will be used to illustrate this method of manufacture.

A first L-shaped radiation guide portion 300 comprises a first 302 and a second 304 elongate member having a major and minor dimension. The first elongate member is connected to the second elongate member along an edge along the major dimension 306 to form a generally "L-shaped" radiation guide portion.

A second L-shaped radiation guide portion 308 comprises a first 310 and a second 312 elongate member having a major and minor dimension. The first elongate member is connected to the second elongate member along an edge along the major dimension 314 to form a generally "L-shaped" radiation guide portion. The first and second radiation guide portions comprise an inner 316 and an outer surface 318.

A gold layer is applied to the inner surface of the first and second L-shaped radiation guide portions by the process of sputtering, well known in the art. It may be necessary to apply a layer of chromium to the inner surface of the L-shaped radiation guide portions. A chromium layer enables the gold to bind strongly to the L-shaped radiation guide portions and may be necessary if the L-shaped radiation guide portions comprise a material with a low affinity for gold.

Figure 10:
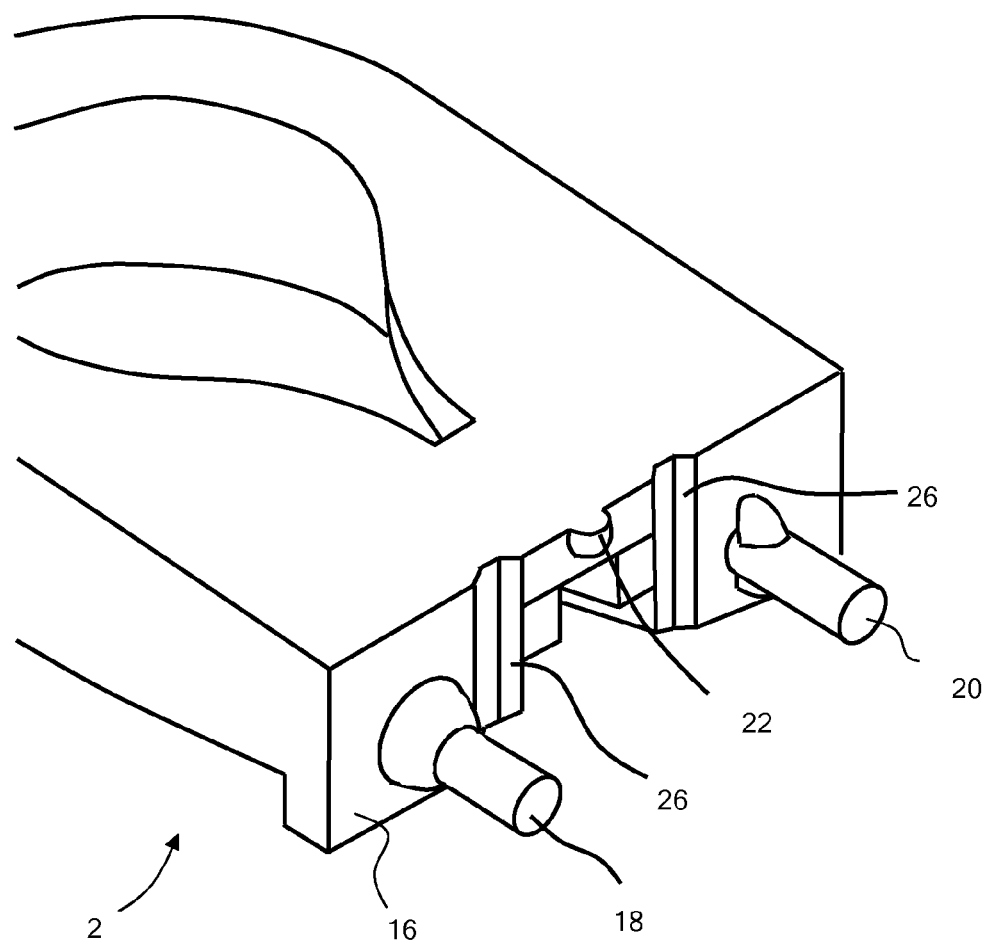
FIG. 10 is a perspective view of the body of the gas sensor.

The first and second L-shaped radiation guide portions are arranged as illustrated in FIG. 10A such that the first L-shaped radiation guide portion is anti-aligned with the second L-shaped radiation guide portion such that a cavity is formed therebetween, and the gold layer is on the interior surface of the hollow body so formed. The edges of the first and second L-shaped radiation guide portions are bonded together by soldering. Alternatively they may be bonded by glue or welding, for example.

In an alternative embodiment the gold layer may be replaced by an aluminium layer or two dielectric layers. In the latter case, a layer of low refractive index, such as ZnS is applied onto a layer of high refractive index, such as $MgF_2$ or $TiO_2$. Whilst an extremely effective reflective material, the application of two dielectric layers requires a high level of precision and is correspondingly expensive.

The above method is in contrast the typical method of manufacture used for radiation guides and sample chambers, wherein a planar member 320 is bonded onto a member comprising a trench 322. A planar surface is straight forward to apply a reflective material to but a to apply a reflective material to the interior surface of a trench is challenging if a smooth finish is to be obtained.

Further variations and modifications may be made within the scope of the invention herein disclosed.

The invention claimed is:

1. A gas sensor comprising a radiation source, a detector operable to detect radiation emitted by the radiation source and a radiation guide operable to guide radiation between the radiation source and the detector, the radiation guide comprising a curved portion having a substantially rectangular cross section, wherein the curved portion of the radiation guide curves around an axis parallel to one of the sides of the rectangular cross section; wherein the radiation guide has an inward facing surface formed from a material operable to reflect radiation emitted by the radiation source, which material absorbs at least 1% of incident radiation.

2. A gas sensor according to claim 1, wherein the substantially rectangular cross section is a substantially oblong cross section having a major and a minor dimension.

3. A gas sensor according to claim 2, wherein the curved portion of the radiation guide curves around an axis parallel to the major dimension of the substantially rectangular cross section.

4. A gas sensor according to claim 1, wherein the radiation guide comprises a collimator operable to at least partially collimate radiation emitted by the radiation source.

5. A gas sensor according to claim 4, wherein the radiation guide comprises a major dimension and radiation emitted by the radiation source is generally collimated by the collimator predominantly in a single direction parallel to the major dimension of the radiation guide.

6. A gas sensor according to claim 4, wherein the collimator comprises a parabolic reflector.

7. A gas sensor according to claim 1, wherein the radiation guide comprises a condenser operable to condense radiation onto the detector.

8. A gas sensor according to claim 7, wherein the radiation guide comprises a major dimension and radiation entering the condenser from the radiation guide is predominantly condensed onto the detector in a single direction parallel to the major dimension of the radiation guide.

9. A gas sensor according to claim 7, wherein the condenser comprises a parabolic reflector.

10. A gas sensor according to claim 1, wherein the radiation source and the detector are adjacent to each other.

11. A gas sensor according to claim 1, wherein the shortest path length of radiation between the radiation source and the detector along the radiation guide is at least ten times the spacing between the radiation source and the detector.

12. A gas sensor according to claim 1, wherein the radiation source and the detector are in thermal communication with each other.

13. A gas sensor according to claim 1, wherein the radiation guide comprises first and second curved portions which curve in opposite senses.

14. A gas sensor comprising a radiation source, a detector operable to detect radiation emitted by the radiation source and a radiation guide operable to guide radiation between the radiation source and the detector; the radiation guide comprising a curved portion having a substantially rectangular cross section, wherein the curved portion of the radiation guide curves around an axis parallel to one of the sides of the rectangular cross section; wherein: the radiation guide comprises a plurality of said curved portions; the radiation guide comprises first and second curved portions which curve in opposite senses; and the radiation guide comprises a first curved portion which curves in a first sense and then a second curved portion, further along the radiation guide than the first curved portion (measured from the radiation source to the detector) which curves in a second opposite sense, and a third curved portion, further along the radiation guide than the second curved portion (measured from the radiation source to the detector) curved in the first sense.

15. A gas sensor according to claim 14, wherein the first and third curved portion each curve in the first sense by at least 10° and the second curved portion, curves in the opposite sense with a substantially constant curve for at least 180°.

16. A gas sensor according to claim 14, wherein the radiation guide has a plane of symmetry.

17. A gas sensor according to claim 14, which changes the mean direction of radiation between the radiation source and the detector by at least 90°.

18. A gas sensor according to claim 14, wherein the integral of the magnitude of the curvature of the radiation guide is at least 90° and less than 720°.

19. A gas sensor according to claim 14, wherein the radiation guide has a recess adjacent the radiation source and/or detector, the radiation source and/or detector having a radiation guide facing surface and an electrical connection on the respective radiation guide facing surface.

20. A gas sensor according to claim 14, wherein the radiation source and the detector are adjacent to each other.

21. A gas sensor comprising a radiation source, a detector opera detect radiation emitted by the radiation source and a radiation guide operable to guide radiation between the radiation source and the detector, the radiation guide comprising a curved portion having a substantially rectangular cross section, wherein the curved portion of the radiation guide curves around an axis parallel to one of the sides of the rectangular cross section; wherein the gas sensor comprises a radiation guide element comprising or consisting of the said radiation guide, and a support element comprising the radiation source and/or the detector, wherein the radiation guide element or the support element may comprise a plurality of locating elements configured to locate the support element relative to the radiation guide element to thereby align the detector and radiation source with the radiation guide.

22. A gas sensor according to claim 21, wherein the radiation guide or the support element comprises three locating elements.

23. A gas sensor according to claim 21, wherein the radiation guide or the support element comprises a biasing means to bias the support element towards the radiation guide element.

24. A gas sensor comprising a support element and a radiation guide element, the support element comprising a radiation source and a detector operable to detect radiation emitted by the radiation source; the radiation guide element comprising a radiation guide operable to guide radiation between the radiation source and the detector; wherein the support element or the radiation guide element comprises a plurality of locating elements configured to locate the support element relative to the radiation guide element to thereby align the radiation source and the detector with the radiation guide.

25. A gas sensor according to claim 24, wherein the gas sensor comprises three locating elements.

26. A gas sensor according to claim 24, wherein the gas sensor comprises a biasing means to bias the support element towards the radiation guide element.

27. A gas sensor comprising a radiation source, a detector operable to detect radiation emitted by the radiation source and a radiation guide operable to guide radiation between the radiation source and the detector, wherein the detector is operable to emit radiation having a different wavelength spectrum to that emitted by the radiation source, and the radiation source is operable to detect radiation emitted by the detector.

28. A gas sensor according to claim 27, further comprising an electronic circuit operable to cause the radiation source and the detector to operate in two modes such that in a first mode the radiation source emits radiation and said radiation is detected by the detector to provide a measurement signal, and in a second mode the detector emits radiation and said radiation is detected by the radiation source to provide a reference signal.

29. A gas sensor according to claim 27, wherein radiation emitted by the detector and detected by the radiation source provides a reference signal and the radiation emitted by the radiation source and detected by the detector provides a measurement signal.

30. A gas sensor according to claim 27, wherein the detector and radiation source emit radiation with different peak wavelengths.

31. A gas sensor according to claim 27 wherein the radiation guide comprises a curved portion having a substantially rectangular cross section, wherein the curved portion of the radiation guide curves around an axis parallel to one of the sides of the rectangular cross section.

32. A gas sensor comprising a first radiation source, a second radiation source, a detector operable to detect radiation emitted by the first radiation source and the second radiation source, and a radiation guide operable to guide radiation from the first radiation source and the second radiation source to the detector, wherein radiation emitted from the second radiation source is guided along a path extending either or both around or through the first radiation source.

33. A gas sensor according to claim 32, wherein the second radiation source emits radiation with a different wavelength spectrum to the first radiation source.

34. A gas sensor according to claim 32, wherein radiation emitted from the second radiation source is guided along a path extending through the first radiation source.

35. A gas sensor according to claim 34, wherein at least 1% of the radiation emitted by the second radiation source is transmitted through the first radiation source.

36. A gas sensor according to claim 32, wherein the substantial majority or all of the radiation from the second radiation source which reaches the detector passes through the first radiation source.

37. A gas sensor according to claim 32, wherein radiation emitted from the second radiation source is transmitted around the first radiation source.

38. A gas sensor according to claim 32, wherein the first and second radiation sources are mounted to opposite sides of a printed circuit board, the printed circuit board comprising a bore therethrough, the first and second radiation sources being located at opposite ends of the bore.

39. A gas sensor according to claim 32, wherein the gas sensor comprises an electronic circuit operable to pulse the first and second radiation sources alternately such that radiation from either the first radiation source or the second radiation source may be detected by the detector.

40. A gas sensor according to claim 32 wherein the radiation guide comprises a curved portion having a substantially rectangular cross section, wherein the curved portion of the radiation guide curves around an axis parallel to one of the sides of the rectangular cross section.

41. A gas sensor comprising a radiation source, a detector operable to detect radiation emitted from the radiation source and a radiation guide having a plurality of reflective walls, wherein the radiation guide is defined by two abutting radiation guide portions having substantially L-shaped reflective surfaces.

42. A method of manufacturing an optical absorption gas sensor comprising two or more L-shaped radiation guide comprising at least one reflective surface and bonding the two or more L-shaped radiation guide portions to form a radiation guide such that the reflective surface of the two or more L-shaped radiation guide portions forms the interior surface of the radiation guide.

43. A gas sensor comprising a support element and a radiation guide element, the support element comprising a radiation source and a detector operable to detect radiation emitted by the radiation source, the radiation guide element comprising a radiation guide having a conductive surface, the radiation source and/or detector having a radiation guide facing surface with an electrical connection on the radiation guide facing surface, the radiation guide comprising a support element facing surface which forms at least part of the conductive surface, and a recess in the support element facing surface adjacent to the radiation source and/or a recess in the support element facing surface adjacent to the detector.

* * * * *